Figure 1:
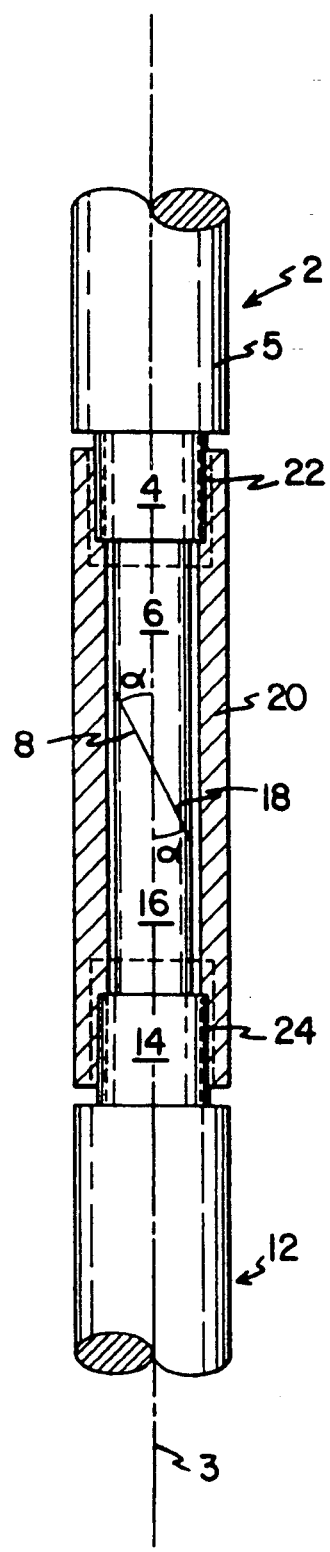

United States Patent [19]

Schelhas

[11] Patent Number: 5,062,849
[45] Date of Patent: Nov. 5, 1991

[54] JOINT FOR COUPLING TWO ELONGATED PROSTHESIS SECTIONS

[75] Inventor: Klaus-Dieter Schelhas, Bremen, Fed. Rep. of Germany

[73] Assignee: Bristol-Myers Squibb Company, New York, N.Y.

[21] Appl. No.: 496,359

[22] Filed: Mar. 20, 1990

[30] Foreign Application Priority Data

Mar. 21, 1989 [DE] Fed. Rep. of Germany ....... 3909182

[51] Int. Cl.$^5$ ............................................. A61F 2/28
[52] U.S. Cl. ...................... 623/16; 623/18; 623/38; 403/341; 606/62; 606/73
[58] Field of Search .................. 623/38, 16, 18; 403/118, 307, 341, 343, 374, 118; 285/355, 421; 606/62, 65, 67, 73

[56] References Cited

U.S. PATENT DOCUMENTS

| | | | |
|---|---|---|---|
| 49,386 | 8/1865 | Cross | 403/307 X |
| 179,764 | 7/1876 | Briggs et al. | 623/38 X |
| 501,110 | 7/1893 | Smith | 403/307 X |
| 3,873,223 | 3/1975 | Caperton | 403/341 |
| 3,979,779 | 9/1976 | Zeibig et al. | 623/16 X |
| 4,938,768 | 7/1990 | Wu | 623/16 |

FOREIGN PATENT DOCUMENTS

| | | | |
|---|---|---|---|
| 327998 | 10/1920 | Fed. Rep. of Germany | 403/341 |
| 3605630 | 9/1987 | Fed. Rep. of Germany | 623/16 |
| 250324 | 4/1926 | United Kingdom | 403/341 |
| 8303450 | 10/1983 | World Int. Prop. O. | 403/341 |

Primary Examiner—Randall L. Green
Assistant Examiner—David H. Willse
Attorney, Agent, or Firm—Merchant & Gould, Smith, Edell, Welter & Schmidt

[57] ABSTRACT

Presented is an arrangement for coupling two rod-shaped prosthesis sections that displays a clamping sleeve having at its ends contrarotating internal threads that can be screwed with corresponding external threads of the prosthesis sections. To prevent loosening of the connection, the free ends of the prosthesis sections are provided with complementary, sloping contact surfaces which, when tightening the clamping sleeve, produce a loaded diagonal thrust and thereby place the screw couplings under load.

4 Claims, 1 Drawing Sheet

JOINT FOR COUPLING TWO ELONGATED PROSTHESIS SECTIONS

DESCRIPTION

The invention concerns an arrangement for coupling two rod-shaped prosthesis sections, with a clamping sleeve that displays at its ends contrarotating internal threads that can be screwed with corresponding external threads of the prosthesis sections.

These types of arrangements are known and serve to join together prostheses assembled from several parts, e.g. prostheses shafts or total prostheses of the human femur. These types of arrangements are additionally employed, in the case of certain indications, for anchoring the shaft of a knee prosthesis or a hip prosthesis on a bone nail that has been installed beforehand in the bone marrow space of the human bone of concern. Besides the desired tension and compression strength, the arrangement must in particular, at the same time, also guarantee that the two prosthesis sections are coupled together in rotation-fast fashion, i.e. joined in non rotatable fashion. It is precisely this rotation-fast, i.e. non rotatable coupling of the two prosthesis sections that, at the same time, represents an essential problem that is only incompletely resolved in the case of known arrangements by the use of additional securing means, such as securing screws, etc.

Therefore, the object of the invention is to further develop the arrangement of the initially mentioned species such that a particularly simple, and at the same time rotation-fast, coupling of the prosthesis sections is guaranteed.

This objective is met in accordance with the invention with the arrangement of the initially mentioned species in that the free ends of the prosthesis sections display sloping contact surfaces that produce a diagonal thrust when the clamping sleeve is tightened, thus sliding over one another.

The advantages of the invention lie particularly in the fact that the free ends of the prosthesis sections display sloping contact surfaces that run against one another and produce a diagonal thrust when the clamping sleeve with its end-side, contrarotating internal threads is screwed with the corresponding external threads of the prosthesis sections, and thereby pulling the prosthesis sections together. In so doing, the sloping contact surfaces move against each other over a desired tightening path and generate counter forces acting in the longitudinal direction that put the threaded connection between clamping sleeve and the prosthesis sections under load and, therefore, prevent the undesired loosening of the screwed connection. Generated in this manner is a self-locking screwed joint between the prosthesis sections and the clamping sleeve without the need for additional securing means, such as transverse pins or securing screws that are likewise subject to the danger of loosening. Since the sloping contact surfaces bear against one another, additionally reliably prevented is a rotatability of the prosthesis sections relative to one another, because the sloping contact surfaces possess no symmetry of rotation to the longitudinal axis of the prosthesis sections.

Particularly preferred, the sloping contact surfaces of the two prosthesis sections are complementary to one another, i.e. they have the same angle of inclination relative to the longitudinal axis of the prosthesis sections and bear flatly against one another when the coupling is tightened.

In accordance with a preferred form of embodiment of the invention, the free ends of the prosthesis sections are constructed as cylindrical pins with a reduced cross section, and the sloping contact surfaces are formed on the cylindrical pins, on their open-face sides. The sloping contact surfaces are preferably formed from a plane that intersects the cylindrical pin at a predetermined angle to the pin longitudinal axis. Depending upon the choice of this angle of intersection, the counter force acting on the joint here is different, which inhibits a loosening of the clamping sleeve.

Particularly preferred, the clamping sleeve has an internal diameter that is only slightly larger than the diameter of the cylindrical pins of the two prosthesis sections. Then when the two sloping contact surfaces are pushed against one another in the longitudinal direction, the cylindrical pins are simultaneously urged outwardly, transversely to the longitudinal direction, against the inner surface of the clamping sleeve and bear against the inner surface of the clamping sleeve in force-locking fashion. In this manner, the connection of the two prosthesis sections is additionally braced inside the clamping sleeve.

In accordance with another preferred form of embodiment of the invention, the screw coupling at one end of the tightening sleeve has a different thread pitch than the screw coupling at the other end of the tightening sleeve, whereby one screw coupling in particular is structured as a fine thread, while the other screw coupling represents a normal thread. This form of embodiment of the invention has the advantage that the locking force of the fine thread is particularly great when tightening the connection and also, in the case of a relatively short tightening path, acts over several thread passes, while on the other hand the normal thread with its corresponding thread pitch allows screwing the clamping sleeve with few turns.

Advantageous further developments of the invention are characterized by the features of the subclaims.

An example of embodiment of the invention is explained in more detail in the following with the aid of the drawing.

The FIGURE shows a cross section through an arrangement in accordance with the invention.

A first rod-shaped prosthesis section 2 has at its free end a threaded pin 6 whose end-side front face is constructed as a sloping contact surface 8. The sloping contact surface 8 is a plane that cuts the longitudinal axis 3 of the prosthesis section 2 at an acute angle α. A second rod-shaped prosthesis section 12 is likewise constructed at its free end as a cylindrical pin 16 whose free front face is also structured as a sloping contact surface 18. The contact surface 18 is likewise flat and cuts the longitudinal axis 3 of the two prosthesis sections 2, 12 at an angle α. At a predetermined distance from the sloping contact surfaces 8, 18, the cylindrical pins 6, 16 each carry an external thread 4, 14.

A clamping sleeve 20 surrounds the cylindrical pins 6, 16 and has at its ends contrarotating internal threads 22, 24, and can be screwed with the corresponding external threads 4, 14 of the prosthesis sections 2, 12 by means of the internal threads 22, 24. The pins 6, 16 have a length such that the sloping contact surfaces 8, 18 bear against one another when the tightening sleeve 20 is screwed with the external threads 4, 14 of the prosthesis sections 2, 12. The internal diameter of the clamping sleeve 20 is only slightly larger than the diameter of the cylindrical pins 6, 16. In the form of embodiment represented, the threads 4, 14 have, relative to the cylindrical pins, a slightly larger diameter and relative to the then following portion of the prosthesis section 2, 12 concerned, a reduced diameter. The external diameter of the clamping sleeve 20 corresponds approximately to the diameter that the prosthesis sections in contact with the external threads 4, 14 have, so that the external diameter remains approximately constant over the entire length of the combination.

The external thread of one prosthesis section and the corresponding internal thread of the clamping sleeve 20 are structured as a fine thread. The external thread of the other prosthesis section and the associated other internal thread of the clamping sleeve 20 are preferably structured as normal threads.

When clamping sleeve 20 is screwed with the prosthesis sections 2, 12, the sloping contact surfaces 8, 18—with appropriate alignment of the prosthesis sections—come to bear against one another and then produce a diagonal thrust. Then, if the clamping sleeve 20 is screwed further onto the external thread 4, 14, the contact surfaces 8, 18 move against one another and, in so doing, are pressed outwardly, transversely to the longitudinal axis 3, against the inner surface of the clamping sleeve. Additionally, when the contact surfaces 8, 18 move against one another, generated are counter forces directed in the axial direction that load the screw connection and inhibit loosening of the clamping sleeve 20, in particular in the case of the fine thread.

The relative displacement that the contact surfaces 8, 18 still pass over after the contact surfaces 8, 18 have come into touching contact is designated as the tightening path. Depending upon the inclination of the sloping contact surfaces 8, 18, a relatively greater tightening path can be realized which, over several turns of the clamping sleeve 20, acts upon the screw coupling with the counter force or tightening force that holds the screw coupling under load and therewith inhibits loosening. In this manner, the screw connection—possibly over several thread passes—is secured against loosening.

I claim:

1. Apparatus adapted to provide a self-locking, non-rotating joint for coupling two rod-shaped prosthesis sections using a hollow clamping sleeve, the apparatus comprising:
    two prosthesis sections, each section having an unthreaded free end and external threads adjacent the free end, each free end being substantially cylindrical and having a sloping contact surface;
    a hollow clamping sleeve with an interior diameter slightly larger than the outer diameter of the free ends, the clamping sleeve having counter-rotating internal threads adapted to cooperate with the external threads of the prosthesis sections, such that the sloping contact surfaces of the prosthesis sections slide on one another when the clamping sleeve is tightened, forcing said free ends transversely against the interior surface of said clamping sleeve; whereby the prosthesis sections are joined in non-rotatable, self-locking manner.

2. Apparatus according to claim 1, wherein the threads cooperating on one prosthesis section have a different pitch than the threads on the other prosthesis section.

3. Apparatus according to claim 1, wherein the threads of the prosthesis sections have a reduced diameter relative to adjacent portions of the prosthesis sections, and that the external diameter of the clamping sleeve corresponds approximately to the diameter of the adjacent portions of the prosthesis sections.

4. Apparatus according to claim 1, wherein there is formed on an external surface of the clamping sleeve a polygon for applying a tightening tool.

* * * * *